United States Patent [19]

Greenwood et al.

[11] Patent Number: 5,708,191
[45] Date of Patent: Jan. 13, 1998

[54] ULTRASONIC FLUID DENSITOMETRY AND DENSITOMETER

[75] Inventors: Margaret S. Greenwood, Richland, Wash.; Jason C. Lail, Conover, N.C.

[73] Assignee: Battelle Memorial Institute, Richland, Wash.

[21] Appl. No.: 628,834

[22] Filed: Apr. 5, 1996

[51] Int. Cl.[6] .................................................. G01N 9/00
[52] U.S. Cl. ............................................................ 73/32 A
[58] Field of Search ........................... 73/32 A, 54.41, 73/861.25, 861.27, 861.28, 597, 644, 628, 290 V; 364/558, 509

[56] References Cited

U.S. PATENT DOCUMENTS

| | | | |
|---|---|---|---|
| 4,149,139 | 4/1979 | Kronk | 340/3 R |
| 4,320,659 | 3/1982 | Lynnworth et al. | 73/589 |
| 4,571,693 | 2/1986 | Birchak et al. | 364/509 |
| 4,821,838 | 4/1989 | Chen | 181/175 |
| 4,893,496 | 1/1990 | Bau et al. | 73/32 A |
| 4,991,124 | 2/1991 | Kline | 364/558 |
| 5,365,778 | 11/1994 | Sheen et al. | 73/54.41 |

OTHER PUBLICATIONS

Research and Development Magazine, Oct., 1994, p. 3.
Sheen, et al., "An In-Line Ultrasonic Viscometer," Review of Progress in Quantitative Nondestructive Evaluation, vol. 14a, pp. 1151–1158, 1995.

*Primary Examiner*—Hezron E. Williams
*Assistant Examiner*—Richard A. Moller
*Attorney, Agent, or Firm*—Paul W. Zimmerman

[57] ABSTRACT

The present invention is an ultrasonic fluid densitometer that uses a material wedge having an acoustic impedance that is near the acoustic impedance of the fluid, specifically less than a factor of 11 greater than the acoustic impedance of the fluid. The invention also includes a wedge having at least two transducers for transmitting and receiving ultrasonic signals internally reflected within the material wedge. Density of a fluid is determined by immersing the wedge into the fluid and measuring reflection of ultrasound at the wedge-fluid interface.

15 Claims, 3 Drawing Sheets

5,708,191

ULTRASONIC FLUID DENSITOMETRY AND DENSITOMETER

This invention was made with Government support under Contract DE-AC06-76RLO 1830 awarded by the U.S. Department of Energy. The Government has certain rights in the invention.

FIELD OF THE INVENTION

The present invention is an apparatus and method for measuring fluid density. More specifically, the invention relies upon acoustic impedance matching of a wedge material and a fluid wherein the wedge material is immersed into the fluid for determination of the density of the fluid.

BACKGROUND OF THE INVENTION

Use of sound waves, specifically ultrasonic sound waves for determining fluid density is well known. An ultrasonic sensor for measuring fluid density was reported by S. Sheen at Argonne National Laboratory. It received a R&D 100 Award in 1994 and a description appeared in the Research and Development magazine in October, 1994, p. 15.

Sheen describes an ultrasonic densitometer (FIG. 1) for measuring a density of a fluid 100. The ultrasonic densitometer has a wedge material 102 wherein the wedge material 102 has at least two sides substantially parallel. A first parallel side 104 has a first ultrasonic transducer 106 mounted thereon and a second parallel side 108 immersable into said fluid whereby a first portion of an ultrasonic signal emanating from said first ultrasonic transducer 106 strikes the second parallel side 108 and reflects back to the first parallel side 104 providing a reflection coefficient. A second portion of the ultrasonic signal propagates through the fluid 100, strikes a second wedge immersed surface 110 and reflects back to the first ultrasonic transducer 106 providing a speed of sound in the fluid. The arm surfaces 112 of the T in contact with air for reference measurements. The T-shaped wedges 102 are mounted through the wall of a pipe 114 so that the fluid 100 within the pipe passes between the immersed surfaces 108, 110 of the two T-shaped wedges 102, 102a. From the reflection coefficient and the speed of sound in the fluid, the density of the fluid is obtained. In a second paper S. H. Sheen, H. T. Chien, and A. C. Raptis, "An In-Line Ultrasonic Viscometer," Review of Progress in Quantitative Nondestructive Evaluation, Vol. 14a, pp 1151–1158, 1995, Sheen specifies that the T-shaped wedge material is aluminum. The second transducer generates shear waves used for determining viscosity. A disadvantage of Sheen's ultrasonic densitometer is that because the wedge material is aluminum, the acoustic impedance of the wedge material is much greater than the acoustic impedance of the fluid so that a substantial change in density (eg. 10%) results in a quite small change in the aluminum/liquid reflection coefficient of about 0.014. Secondarily, the ultrasonic signal is required to reflect through the fluid of interest thereby requiring the requisite target surface of a second T-shaped wedge. Further, for fluids attenuative of ultrasound, density measurements would not be obtainable.

Another ultrasonic fluid meter is described in M. S. Greenwood, J. L. Mai, and M. S. Good, "Attenuation measurement of ultrasound in a kaolin-water slurry: A linear dependence upon frequency, " J. Acoust. Soc. Am. 94, 908–916 (1993). This ultrasonic attenuation sensor was developed for concentration measurements in a 1/12-scale model of a double-shell tank. Because fluid density is a function of concentration, this unit may be used to determine fluid density as well as fluid concentration. The sensor consists of a send transducer and a receive transducer, separated by 4 inches. The ultrasound produced by the send transducer travels through a liquid (or slurry) where it is attenuated. The signal recorded by the receive transducer indicates how much attenuation has occurred. However, the instrument required calibration by making measurements in the laboratory for that specific slurry formulation so that concentration of the slurry could be correlated with voltage of signal in receive transducer. Again, this ultrasonic densitometer required that the ultrasonic signal be detected after passing through the fluid, in this case slurry, of interest and further required prior laboratory calibration.

Commercially available ultrasonic fluid concentration measuring devices are available through JM Science Inc, Buffalo, N.Y., Manufactured by: Fuji Ultrasonic Engineering Co., Ltd. In operation, an ultrasonic transducer produces ultrasound that propagates through the fluid of interest then is reflected by a metal plate about an inch away from the transducer. The reflected signal returns to the transducer and the time for a round trip is determined. Since the distance is known, the velocity of ultrasound in the liquid can be determined. The Fuji sensor correlates the speed of sound with a concentration of a particular fluid solution and with temperature of the particular fluid solution and requires laboratory calibration. As with Greenwood et al., the reflected ultrasonic signal must pass through the fluid of interest and the instrument requires calibration.

There is a need in the field of ultrasonic densitometry for an ultrasonic fluid densitometer that has greater sensitivity, does not require calibration and does not require a reflected signal to pass through the fluid of interest.

SUMMARY OF THE INVENTION

The present invention is an ultrasonic fluid densitometer that uses a material wedge having an acoustic impedance that is near the acoustic impedance of the fluid, specifically less than a factor of 11 greater than the acoustic impedance of the fluid. The invention also includes a wedge having at least two transducers for transmitting and receiving ultrasonic signals internally reflected within the material wedge. Density of a fluid is determined by immersing the wedge into the fluid and measuring reflection of ultrasound at the wedge-fluid interface.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
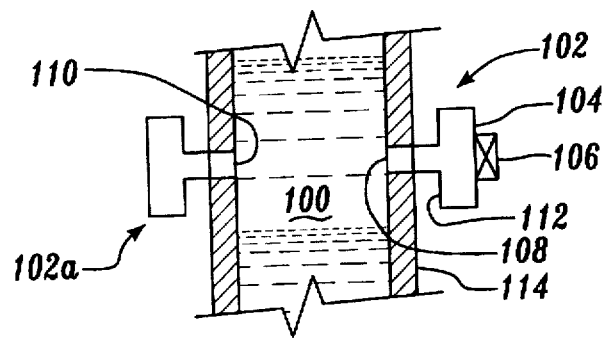
FIG. 1 is a cross section of a prior art ultrasonic densitometer.

The improvement, according to the present invention is that the fluid 100 and the wedge material 102 have a ratio of an acoustic impedance of the wedge material to an acoustic impedance of the fluid that is less than 11. Table 1 shows acoustic impedances for candidate wedge materials and ratio of acoustic impedance of those materials to the acoustic impedance of water which has an acoustic impedance of $1.5(10^6)$ kg/m$^2$s. By using a wedge material 100 having an acoustic impedance ratio to the fluid of less than 11, there is an increased change in reflection coefficient which increases the sensitivity of the ultrasonic densitometer. Specifically for Rexolite (C-LEC Plastics, Inc. Beverly, N.J.), for a 10% change in fluid density, there is a change of about 0.05 of the reflection coefficient.

TABLE 1

| | Acoustic Impedances | |
|---|---|---|
| Material | Acoustic Impedances (kg/m$^2$s) | Ratio to Water |
| Aluminum | 17 (10$^6$) | 11.33 |
| Lead | 25 (10$^6$) | 16.67 |
| Steel | 45 (10$^6$) | 30.00 |
| Rexolite | 2.5 (10$^6$) | 1.67 |

It is preferred that the acoustic impedance ratio be less than about 5 and more preferably less than about 3 when the fluid is a liquid. Plastic includes polymers including but not limited to Rexolite, Loren (Sigma Transducers, Kennewick, Wash.), and acrylics.

Fluids that can be measured are preferably liquid. A liquid may be a liquid solution, or mixture having solid particles or immiscible phases. Immiscible phases include liquids and gases. In mixtures, it is preferred that the non-soluble phase be of a size smaller than a wavelength of the ultrasonic waves. It is further preferable that the mixture be homogenous and may require mixing. When a gas (eg air) phase is present, it is preferred to use a minimum measurement in a series of measurements to obtain the most accurate measure of density. The reason is that gas bubbles may adhere to the surface of the immersed wedge material and increase the reflectance of ultrasound at the wedge material-gas interface.

A further advantage is realized when all detected ultrasonic signals are detected on the basis of ultrasonic reflections internal to the wedge material. More specifically, the present invention further includes embodiments shown in FIG. 2 and FIG. 3. The wedge material 102 has at least two sides substantially parallel. A first parallel side 104 has a first ultrasonic transducer 106 mounted thereon and a second parallel side 108 immersable into said fluid whereby a first portion of an ultrasonic signal emanating from said first ultrasonic transducer 106 strikes the second parallel side 108 and reflects back to the first parallel side 104. The wedge material 102 further has (a) a first non-parallel side 200, 300 from which emanates a second reflected ultrasonic signal toward a second non-parallel side 202; and (b) a receiving ultrasonic transducer 204 mounted on the second non-parallel side 202 for receiving the second reflected ultrasonic signal.

Figure 2:
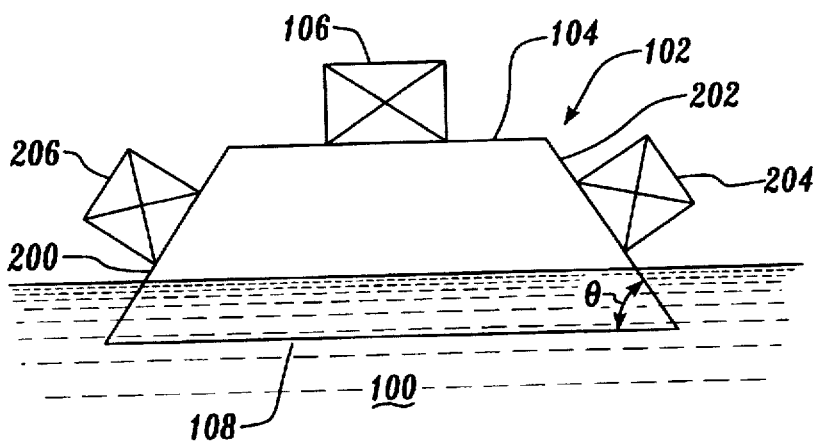
FIG. 2 is a three transducer embodiment of the present invention.

In FIG. 2, each of the first and second non-parallel sides 200, 202 is connected to the first and second parallel sides 104, 108. A transmitting transducer 206 is mounted on the first non-parallel side 200 whereby the transmitting transducer transmits said second ultrasonic signal that reflects from said second parallel side 108 creating the second reflected ultrasonic signal that is received by the receiving transducer 204.

Figure 3:
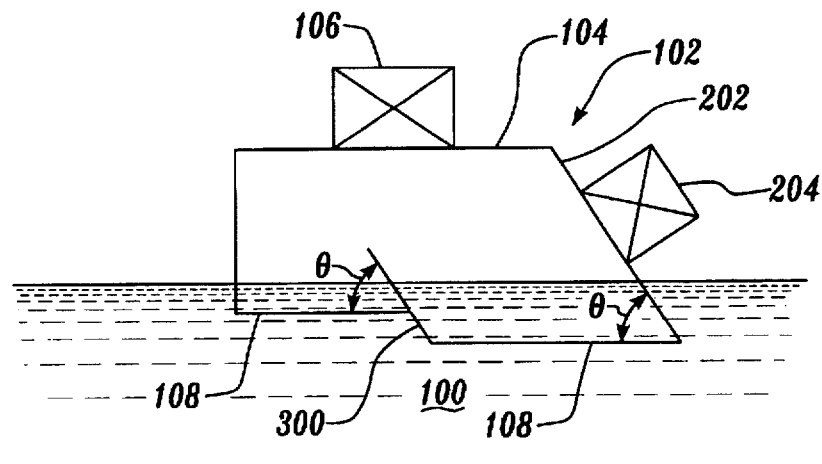
FIG. 3 is a two transducer embodiment of the present invention.

In FIG. 3, the first non-parallel side 300 is a cut in the second parallel side 108 and the second non-parallel side 202 is connected to the first and second parallel sides 104, 108, whereby an ultrasonic signal transmitted by the first transducer is reflected by both the second parallel side 108 and the first non-parallel side 300 producing a reflected signal from the second parallel side 108 to the first transducer and producing said second reflected signal from the first non-parallel side 300 to the receiving transducer 204. For the embodiments shown in FIGS. 2 and 3, it is necessary to know a-priori the speed of sound in the wedge material 100 and the sign (positive or negative) of the reflection coefficient for the wedge material/fluid combination.

The angle theta of the non-parallel sides 200, 202, 300 to the second parallel side 108 is critical to the present invention for sensitivity to small changes in fluid density. An angle of 20 degrees provided limited sensitivity whereas an angle of about 60 degrees provided greater sensitivity to changes in fluid density. Accordingly, the angle theta is preferably greater than about 20 degrees and more preferably greater than about 30 degrees.

Figure 4:
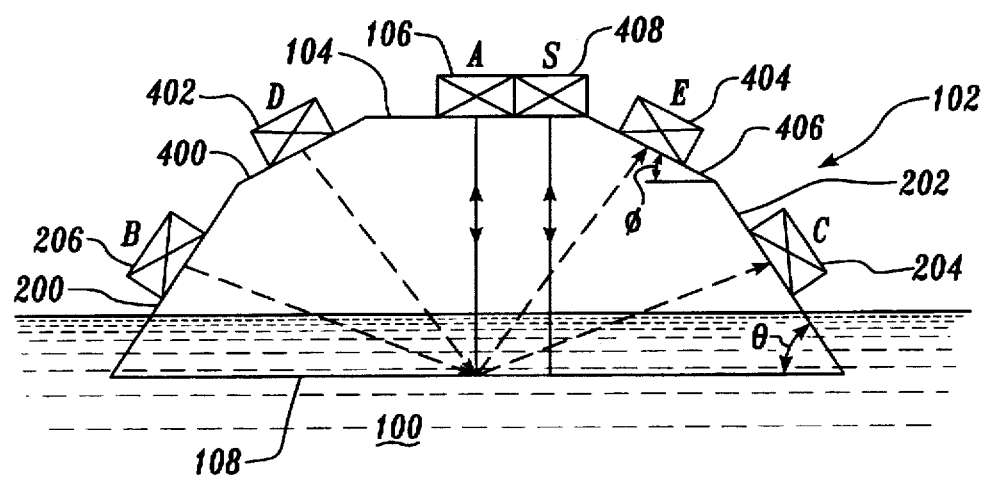
FIG. 4 is a six transducer embodiment of the present invention.

An additional embodiment of the present invention is shown in FIG. 4. This embodiment is similar to the one shown in FIG. 2 but having additional sides and transducers permitting in-situ measurement of speed of sound in the wedge material and in-situ determination of the sign of the reflection coefficient. More specifically, a third non-parallel side 400 has a second transmitting ultrasonic transducer 402 that emits a third ultrasonic signal that reflects from the second parallel side 108 and creates a third reflected ultrasonic signal that is received by a second receiving ultrasonic transducer 404 mounted on a fourth non-parallel side 406. The third and fourth non-parallel sides 400, 406 make a second angle phi with said first parallel side different from the first angle theta. These additional sides and transducers are used to determine the sign of the reflection coefficients. Alternatively, analysis of signal phase may be done to determine the sign of the reflection coefficient without using the second transmitting and receiving transducers 402, 404. However, additional electronic circuitry and possibly additional software for data reduction would be needed for analysis of signal phase, which is less preferred. A fourth transmitting ultrasonic transducer 408 is mounted on the first parallel side 104 for determination of the speed of sound of the shear wave in the wedge material 102. The speed of sound of the longitudinal wave is measured by the pulse-echo measurement or by a pitch-catch measurement.

The transducers may be any ultrasonic transducers, preferably emitting in a range from about 0.5 MHz to about 10 MHz.

Electrical signals from the transducers may be collected for analysis in at least two ways. In one way, A function generator (not shown) may be applied to the transmitting transducer 206. The ultrasound reflected at the second parallel side 108 of the wedge material 102 produces a response in the receive transducer 204. This RF-signal, after amplification (or attenuation) by a receiver (not shown) may be sent to a peak detector (not shown). After selecting a window around the RF-signal of interest, the peak detector outputs a DC-voltage that is proportional to the maximum of the RF-voltage in the window.

Alternatively, a 12-bit digitizer may be used so that extremely small changes in the voltage can be detected. When a 12-bit digitizer is used, the maximum value of the signal will be determined using software. A multiplexer system will sequentially send the toneburst signal to each send transducer and obtain the return signal. An algorithm will be developed to take averages and, in the case of the slurry, to look for minimum values in the signal and to process this data to produce an on-line value of the density and velocity of sound.

EXAMPLE 1

Figure 5A:
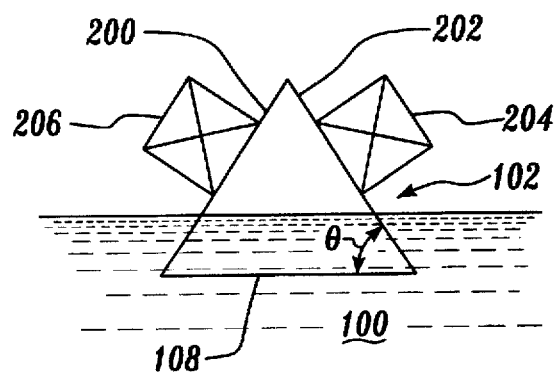
FIG. 5a is a pitch-catch block for experiments.
Figure 5B:
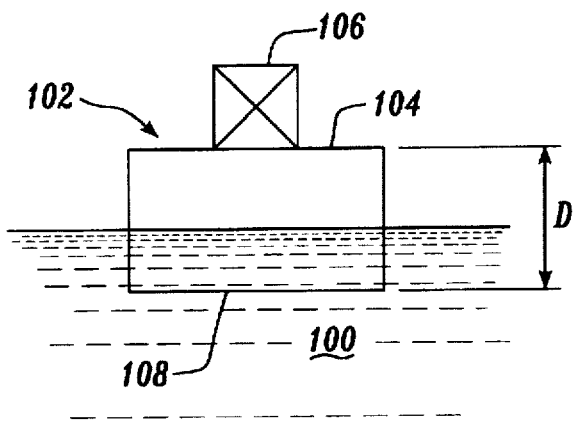
FIG. 5b is a pulse-echo block for experiments.

An experiment was conducted to demonstrate the ultrasonic densitometer of the present invention. For the experiment, two wedges were used. FIG. 5a and FIG. 5b shows the experimental setup for the pitch-catch mode, FIG. 5a, and the pulse-echo mode, FIG. 5b. The wedge material 102 is Rexolite. For the pitch-catch, FIG. 5a, the wedge material is an equilateral triangular solid with an angle theta of about 60 degrees. For the pulse-echo, FIG. 5b, the distance D between the first transducer 106 and the second parallel side 108 was 2.7 cm.

A 12-cycle toneburst at a frequency of 2.25 MHz, produced by the Wavetek 901 function generator, was applied to the transmitting transducer 206. The ultrasound reflected at the second parallel side 108 of the wedge material 102 produced a response in the receive transducer 204. This produced an RF-signal, after amplification (or attenuation) by an MR101 receiver, was sent to a Panametrics GPD-5052 peak detector. After passing through an RC circuit with a time constant of 10 milliseconds to minimize fluctuations, the DC voltage was measured by a DC-voltmeter to an accuracy of three decimal places.

The reflection coefficient was determined by comparing the amplitude of the RF-voltage (or toneburst) of the received signal (or echo) when the second parallel side 108 of the wedge material 102 is immersed in the liquid with that when it is air. Since the voltage of the received signal is directly proportional to the pressure and to the reflection coefficient, the following relationship is obtained:

$$RC_{liq} = RC_{air}(V_{liq}/V_{air})$$

where

RC is reflection coefficient, and

V is voltage from the transducer.

The reflection coefficient is a function of (1) density of the wedge material 102, (2) speed of sound of the longitudinal wave, (3) speed of sound of the shear wave, (4) the angle of incidence of the longitudinal wave with respect to the second parallel side 108, (5) the density of the fluid, and (6) the speed of sound in the fluid (See J. Krauthkramer and H. Krauthkramer, *Ultrasonic Testing of Materials*, SpringerVerlag, Third Edition, 1983, pp 606–607, Equation A.10). By obtaining measurements at two angles, pulse echo at zero degrees and pitch-catch at another angle, two equations for the reflection coefficients are provided having the unknowns of density of the fluid and speed of sound in the fluid.

The speed of sound in Table E-1 was measured using the time-of-flight method having an uncertainty of about 2%.

The fluid used in this experiment was water with varying amounts of sugar. Samples 2–8 received increasing amounts of sugar. The sugar was commercially available cane sugar. Table E-1 shows the density obtained by weighing fluid samples in a 50-ml volumetric flask. Table E-1 also shows the voltage ratio data for reflection coefficients obtained using the pulse-echo block and the pitch-catch block with a 60 degree angle. In each case an average DC-voltmeter reading was obtained when the interface was immersed in the liquid and when in air. From this voltage ratio data, the reflection coefficients were derived.

TABLE E-1

Parameter Standards For Water Samples

| Sample | Sugar Conc. | Density kg/m$^3$ | Speed of Sound (m/s) | Pitch-Catch $V_{liq}/V_{air}$ | Pulse-echo $V_{liq}/V_{air}$ |
|---|---|---|---|---|---|
| 1 | 0.00 | 997 | 1483 | 0.3245 | 0.2477 |
| 2 | >0.00 | 1011 | 1498 | 0.3454 | 0.2380 |
| 3 | >0.00 | 1024 | 1510 | 0.3625 | 0.2287 |
| 4 | >0.00 | 1036 | 1523 | 0.3802 | 0.2193 |
| 5 | >0.00 | 1055 | 1537 | 0.4052 | 0.2066 |
| 6 | >0.00 | 1060 | 1542 | 0.4133 | 0.2016 |
| 7 | >0.00 | 1070 | 1554 | 0.4265 | 0.1942 |
| 8 | >0.00 | 1087 | 1567 | 0.4514 | 0.1805 |

The objective is to convert the pulse-echo at zero degrees and pitch-catch at 60 degrees RF-voltage ratios to reflection coefficients, solve the inverse problem to obtain the density and velocity of sound in the liquid, and compare them with the densities and velocities of sound shown in Table E-1.

The reflection coefficient is very sensitive to the longitudinal wave velocity and the shear wave velocity. This sensitivity has been used to determine these velocities to four significant figures. These values will be used in all further calculations: longitudinal wave velocity in Rexolite $C_L$=2337 m/s, shear wave velocity in Rexolite $C_T$=1157 m/s.

A reflection coefficient is obtained by multiplying the RF-voltage ratio by the reflection coefficient for air. The reflection coefficient for air at 0° is −1.00 and at 60°, +0.4170. Table E-2 give the ultrasonically derived velocities of sound and densities of the eight liquid samples.

TABLE E-2

Ultrasonically Derived Parameters

| Sample | Speed of Sound (m/s) | % error | Density (kg/m$^3$) | % error |
|---|---|---|---|---|
| 1 | 1481 | −0.13% | 988.0 | 0.10% |
| 2 | 1498 | 0.00% | 1007.0 | −0.44% |
| 3 | 1503 | −0.45% | 1024.2 | −0.02% |
| 4 | 1510 | −0.85% | 1039.6 | 0.33% |
| 5 | 1522 | −0.98% | 1059.1 | 0.40% |
| 6 | 1519 | −1.50% | 1072.1 | 1.10% |
| 7 | 1522 | −2.10% | 1086.8 | 1.61% |
| 8 | 1527 | −2.60% | 1114.8 | 2.60% |

There is very good agreement between the two sets of measurements. These results show that using two reflection coefficients is a viable method for determining the density and the velocity of sound in an aqueous solution to an accuracy of at least 3%.

EXAMPLE 2

An experiment was conducted to use the present invention with non-aqueous liquids. The same apparatus as described in Example 1 were used. Results are shown in Table E-3

TABLE E-3

Non-aqueous liquids

| Sample | Liquid | Density (kg/m$^3$) | Density Error | Speed of Sound (m/s) | Sound Error |
|---|---|---|---|---|---|
| 9 | 2-propanol | 782.6 | −0.72% | 1157.3 | −1.4% |
| 10 | paraffin | 877.2 | 3.12% | 147.6 | −6.6% |

TABLE E-3-continued

Non-aqueous liquids

| Sample Liquid | Density (kg/m³) | Density Error | Speed of Sound (m/s) | Sound Error |
|---|---|---|---|---|
| oil | | | | |

Reasonable agreement was achieved with non-aqueous fluids.

EXAMPLE 3

An experiment was conducted to demonstrate measuring the average bulk density of an aqueous slurry with the present invention. The apparatus described in Example 1 was used.

A slurry was mixed using Potter's silicon dioxide particulate (Type 13) in water. The particulate had a maximum diameter of 0.00381 cm. For ultrasound produced by a 2.25 MHz transducer, the wavelength in water is 0.066 cm. Since the resolution of a wave is approximately equal to its wavelength, the ultrasound should not be able to resolve individual particles in this slurry and measurements should, therefore, determine the average density and average velocity of sound.

The slurry was placed in a 2000 ml beaker and a mixer kept the slurry from settling. The slurry had a density of 1143.1 kg/m³.

Calculations of ultrasonic data were carried out for the slurry and yielded a density of 988 kg/m³, which is 13.6% low compared to the actual density. The source of the problem seemed to be that the mixer was aerating the slurry. The wedge material was re-oriented to a vertical position to minimize accumulation of air bubbles. In addition, the method of taking the measurements was altered. Instead of taking the average value of the voltmeter readings, the minimum value that repeated within a 30–60 second interval (to the second decimal place) was recorded. This reading would correspond to a minimum effect due to air and would give a truer reading of the slurry's non-aerated density.

Additional slurry samples were then subjected to the modified experimental procedure with results shown in Table E-4.

TABLE E-4

Slurry Sample Density Data

| Sample | Density (kg/m³) | Ultrasonic Density (kg/m³) | Percent Error |
|---|---|---|---|
| S-1 | 1143.1 | 1083.2 | −5.24% |
| S-2 | 1097.3 | 1069.9 | −2.49% |
| S-3 | 1077.0 | 1049.8 | −2.52% |
| S-4 | 1050.4 | 1051.6 | 0.11% |
| S-5 | 1037.6 | 1041.3 | 0.36% |
| S-6 | 1065.5 | 1.53.6 | −1.11% |

There is only one sample with an error at about 5%. All other samples are within 3%.

EXAMPLE 4

Using the Rexolite wedge materials as in Example 1, (FIG. 5a and FIG. 5b) and glycerine as the fluid, it was discovered that the pulse-echo signal was so weak as to be essentially non-existent. This was because the acoustic impedance of glycerine nearly matches the acoustic impedance of Rexolite ($2.5(10^6)$kg/m²s). Accordingly, a different plastic material would be used for the pulse-echo wedge material.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An ultrasonic densitometer for measuring a density of a fluid, said ultrasonic densitometer having at least one wedge material, said at least one wedge material having at least two sides substantially parallel, a first parallel side having a first ultrasonic transducer mounted thereon and a second parallel side immersible into said fluid whereby an ultrasonic signal emanating from said first ultrasonic transducer strikes said second parallel side and reflects back to said first parallel side; the improvement comprising:

(a) a first non-parallel side from which emanates a second reflected ultrasonic signal toward a second non-parallel side; and (b) a receiving ultrasonic transducer mounted on said second non-parallel side for receiving said second reflected ultrasonic signal.

2. The ultrasonic densitometer as recited in claim 1, wherein each of said first and second non-parallel sides is connected to said first and second parallel sides.

3. The ultrasonic densitometer as recited in claim 2, further comprising:

a transmitting transducer mounted on said first non-parallel side whereby said transmitting transducer transmits said second ultrasonic signal that reflects from said second parallel side creating said second reflected ultrasonic signal that is received by said receiving transducer.

4. The ultrasonic densitometer as recited in claim 1, wherein said first non-parallel side is a cut in said second parallel side and said second non-parallel side is connected to said first and second parallel sides, whereby an ultrasonic signal transmitted by said first transducer is reflected by both the second parallel side and said first non-parallel side producing a reflected signal from said second parallel side to the first transducer and producing said second reflected signal from said first non-parallel side to said receiving transducer.

5. The ultrasonic densitometer as recited in claim 1, wherein said at least one wedge material is a plastic and said fluid has an aqueous phase.

6. The ultrasonic densitometer as recited in claim 1, further comprising:

(a) a transmitting ultrasonic transducer mounted on said first non-parallel side that emits a second ultrasonic signal that reflects from said second parallel side thereby creating said second reflected ultrasonic signal, said first and second non-parallel sides making a first angle with said first parallel side; and (b) a third non-parallel side having a second transmitting ultrasonic transducer that emits a third ultrasonic signal that reflects from said second parallel side and creating a third reflected ultrasonic signal that is received by a second receiving ultrasonic transducer mounted on a fourth non-parallel side, said third and fourth non-parallel sides making a second angle with said first parallel side different from said first angle.

7. The ultrasonic densitometer as recited in claim 6, further comprising:

a fourth transmitting ultrasonic shear wave transducer mounted on said first parallel side.

8. The ultrasonic densitometer as recited in claim 1, wherein said second non-parallel side forms an angle with said second parallel side, said angle at least 20 degrees.

9. The ultrasonic densitometer as recited in claim 8, wherein said angle is 60 degrees.

10. The ultrasonic densitometer as recited in claim 1, wherein said first and second non-parallel sides are on a first wedge and said first and second parallel sides are on a second wedge.

11. A method of measuring density of a fluid ultrasonically, comprising the steps of:

(a) providing at least one wedge material, said at least one wedge material having at least two sides substantially parallel, mounting a first ultrasonic transducer on a first parallel side and immersing a second parallel side into said fluid and emanating an ultrasonic signal from said first ultrasonic transducer, said ultrasonic signal striking said second parallel side and reflecting back to said first parallel side; wherein the improvement comprises:

(b) emanating a second reflected ultrasonic signal from a first non-parallel side toward a second non-parallel side; and (c) receiving said second reflected ultrasonic signal with a receiving ultrasonic transducer on said second non-parallel side.

12. The method as recited in claim 11, wherein each of said first and second non-parallel sides is connected to said first and second parallel sides.

13. The method as recited in claim 11, wherein said first and second non-parallel sides are on a first wedge and said first and second parallel sides are on a second wedge.

14. The method as recited in claim 11, wherein said second non-parallel side forms an angle with said second parallel side, said angle at least 20 degrees.

15. The method as recited in claim 14, wherein said angle is 60 degrees.

* * * * *